US00PP30346P2

(12) United States Plant Patent
Hansen

(10) Patent No.: US PP30,346 P2
(45) Date of Patent: Apr. 2, 2019

(54) ***KNIPHOFIA* PLANT NAMED 'POKER FACE'**

(50) Latin Name: *Kniphofia hybrida*
Varietal Denomination: Poker Face

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/932,530

(22) Filed: Mar. 12, 2018

(51) Int. Cl.
*A01H 5/02* (2018.01)

(52) U.S. Cl.
USPC ..... Plt./443

(58) Field of Classification Search
USPC ..... Plt./443
See application file for complete search history.

*Primary Examiner* — Annette H Para

(57) ABSTRACT

A new and distinct cultivar of Red Hot Poker plant named *Kniphofia* 'Poker Face' with gracefully-arching, strap-like, keeled, glaucous, gray-green foliage and numerous scapes beginning in early summer and repeating though early fall. Flowers are bright orange, densely arranged on scapes up to 82 cm tall. The new plant is useful for landscaping as a specimen, en masse, as a container plant, or as a long-lasting cut flower.

2 Drawing Sheets

Botanical classification: *Kniphofia hybrida.*
Variety denomination: 'Poker Face'.

BACKGROUND AND ORIGIN OF THE PLANT

The present invention relates to the new and distinct Red Hot Poker, *Kniphofia* 'Poker Face' hybridized under the direction of the inventor at a wholesale perennial nursery in Zeeland, Mich., USA. The new plant was the result of a single seedling selection from a cross of 'Echo Rojo' U.S. Plant Pat. No. 22,791 as the female parent as the female parent and 'Papaya Popsicle' U.S. Plant Pat. No. 22,915 as the male parent as the male parent in 2012. The plant passed initial evaluation in the summer of 2014 and was subsequently given the breeder code KNIF-12-5. *Kniphofia* 'Poker Face' has been successfully asexually propagated by garden rhizome division method since 2014 at the same wholesale perennial nursery in Zeeland, Mich. and subsequently by shoot tip tissue culture, and both methods have been found to be stable and produce identical plants that maintain the unique characteristics of the original plant through multiple generations.

No plants of *Kniphofia* 'Poker Face' have been sold, in this country or anywhere in the world, with this name or any other name, prior to the filing of this application, nor has any disclosure of the new plant been made prior to the filing of this application except that which was disclosed within one year of the filing of this application and was either derived directly or indirectly from the inventor.

SUMMARY OF THE PLANT

*Kniphofia* 'Poker Face' differs from its parents as well as all other *Kniphofia* known to the applicant. The most similar known *Kniphofia* cultivars are the female parent 'Echo Rojo', 'Mango Popsicle' U.S. Plant Pat. No. 22,968, the male parent 'Papaya Popsicle' and 'Poco Orange' U.S. Plant patent application Ser. No. 14/545,806. 'Echo Rojo' is slightly taller in scape height but more reddish in flower color and the new plant is more persistent in the Michigan landscape. 'Mango Popsicle' is shorter in scape and foliage height with more yellow-orange flower color. 'Papaya Popsicle' is shorter in scape and foliage height with deeper orange flower color. 'Poco Orange' is smaller in scape height, foliage height and overall habit and has a lighter orange flower color.

*Kniphofia* 'Poker Face' differs from these above cultivars and all cultivars known to the inventor in that it has:

1. Gracefully arching, strap-like, keeled, gray-green foliage.
2. Rapidly growing, dense habit, winter-hardy, heat and low moisture tolerant, rabbit and deer tolerant, large-sized clumps.
3. Numerous spikes of medium orange flowers on tall stems lightening in maturity;
4. Flowering beginning the first week of summer and repeating into early October in Michigan.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
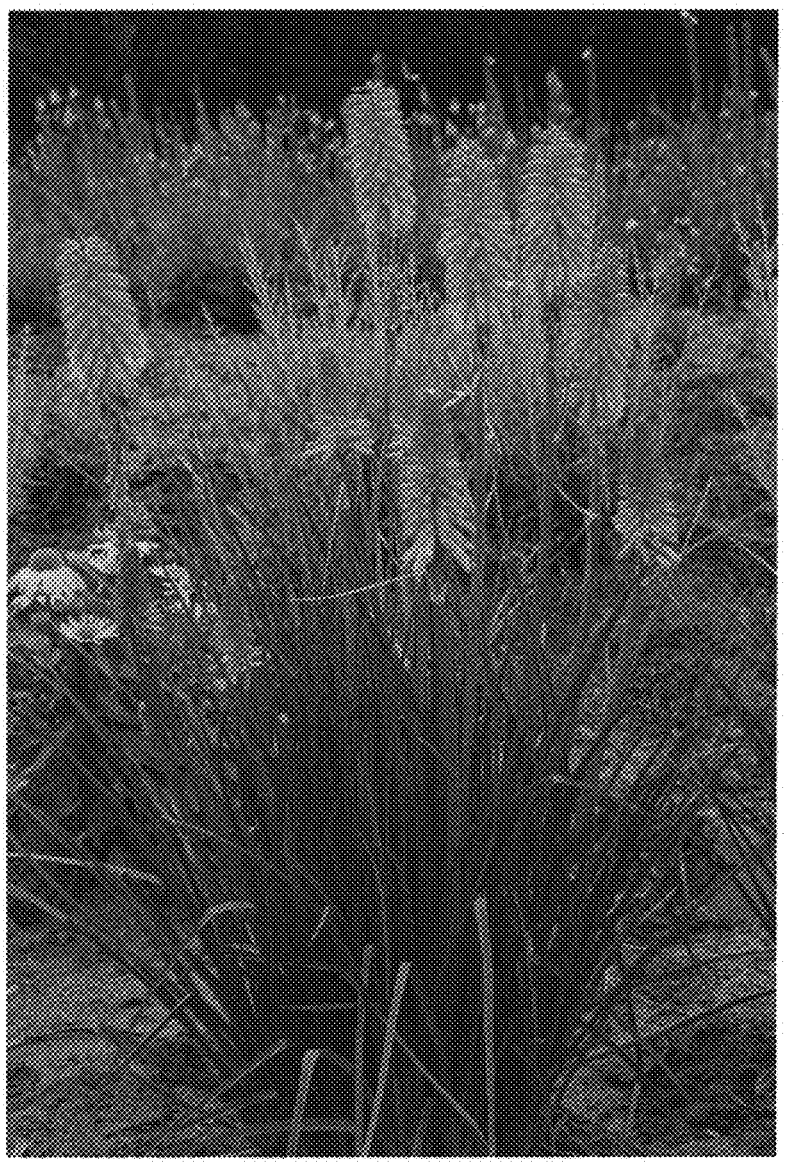
FIG. 1 shows the side-view habit of a three-year-old plant in midseason.
Figure 2:
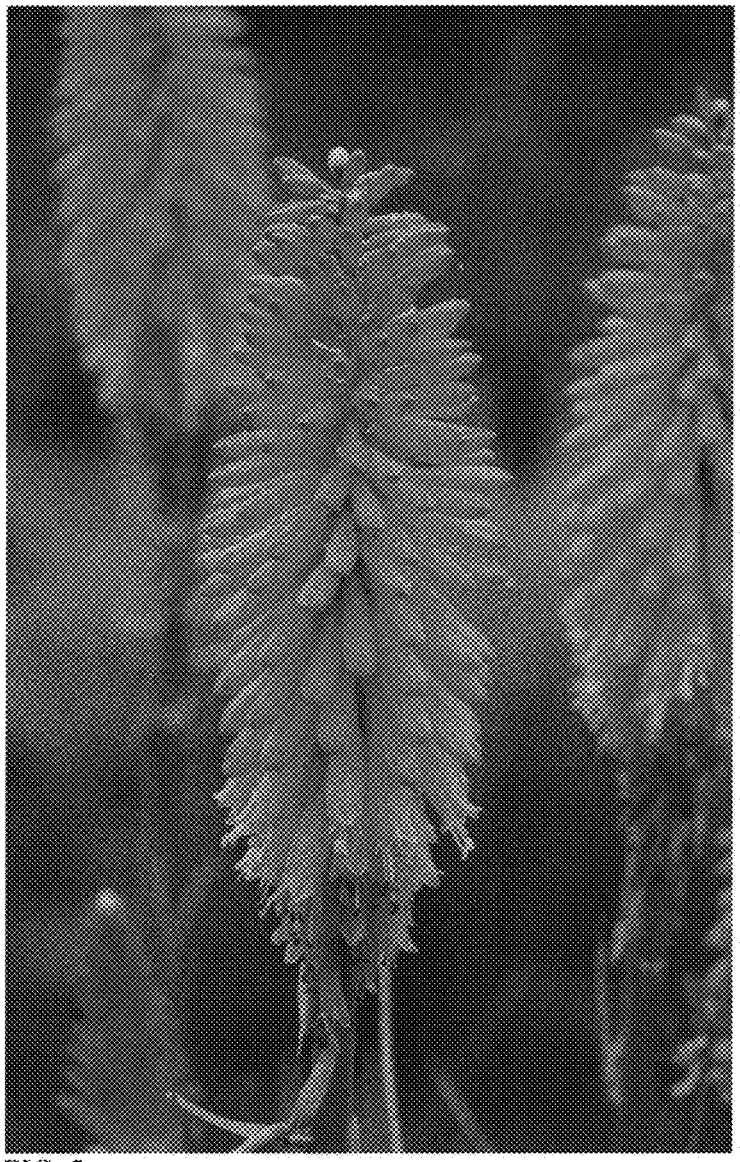
FIG. 2 shows a close-up of the flowers and buds.

The following descriptions and color references are based on the 2015 edition of The Royal Horticultural Society Colour Chart except where common dictionary terms are used. The new plant, *Kniphofia* 'Poker Face', has not been observed under all possible environments. The phenotype may vary slightly with different environmental conditions, such as temperature, light, fertility, moisture and maturity levels, but without any change in the genotype. The following observations and size descriptions are of a four-year-old plant in a trial garden of a wholesale perennial nursery in Zeeland, Mich. under full sun with supplemental water and fertilizer as needed.

Botanical classification: *Kniphofia* hybrid;

Parentage: Proprietary unreleased selection of *Kniphofia* (not patented) as the female or seed parent and the male or pollen parent is unknown;

Propagation method: By garden division of the rhizome;

Growth rate: Vigorous, flowering in 3.5 liter containers in about 10 to 12 weeks from a 25 mm plug liner in late winter to spring and from a one-year-old bare root plant to flowering in 6 to 8 weeks in a 4.0 liter container;

Rooting habit: Fibrous from base of rhizomes, lightly branching; color nearest RHS 158C;

Plant description: Dense, rhizomatous, acaulescent, perennial clump with long thin foliage to about 100.0 cm across and about 68.0 cm tall; flowering to about 82.0 cm tall;

Leaves: Linear; keeled; arranged about 10 leaves per basal division; apex narrowly acute; base truncate, clasping; margin entire; no fragrance observed;

Leaf size: To about 70.5 cm long and 17.0 mm across at base, average about 67.0 cm long and 16.0 mm across at base;

Leaf color: Mature and expanding leaves same; both surfaces nearest RHS 137A;

Leaf venation: Parallel; color same as leaf abaxial and adaxial;

Stem: Acaulescent; rhizome about 28.0 mm across at base;

Inflorescence: In spike-like raceme; about 150 to 180 flowers per stem; about 60 to 80 peduncles per plant; flowering portion about 14.0 cm tall and about 5.4 cm across; lasting about three weeks; flower spacing less than 1.0 mm apart on raceme;

Peduncle: Terete; glabrous; glaucous; to about 82.0 cm long and 14.0 mm diameter;

Peduncle color: Nearest RHS 139D proximally and blushed with nearest RHS 167D distally;

Buds one day prior to opening: Ellipsoidal to tubular with swollen apex; glabrous; lustrous; about 20.0 mm long and about 3.0 mm diameter at base and 6.0 mm diameter at widest point near apex; apex subacute; base rounded;

Bud attitude: Beginning outwardly and drooping as maturing toward anthesis;

Bud color: Nearest RHS N34B becoming nearest RHS 24B in main portion with midrib nearest RHS 33A and secondary veins nearest RHS N25B;

Flowers: Cylindrical forming tubular corolla; perfect; actinomorphic; individually open and effective about three to four days;

Corolla size: To about 21.0 mm long, fused in basal 18.0 mm; face to about 12.0 mm tall and about 8.0 mm wide; tube about 4.0 mm diameter near base and 8.0 mm near throat;

Flower attitude: Drooping;

Flower fragrance: None detected;

Flowering period: Individual racemes effective for about 3 weeks; beginning early summer Michigan for about six week, then continuing with repeat racemes until early fall with a short two week break in the heat of the summer;

Tepals: Six, in two sets of three; both sets with acute apices and fused in basal 18.0 mm forming tube; margin entire; glabrous and lustrous abaxial and adaxial; about 21.0 mm long and about 5.1 mm across just above fusion point;

Tepal color (young abaxial): Distal 3.0 mm of outer tepal set nearest RHS 33A; inner set with 1.0 mm margin of RHS 11D; both sets with midrib nearest RHS 33A and main portion nearest RHS 21D toward base and distally nearest RHS 33B;

Tepal color (young adaxial): Distal 3.0 mm of outer tepal set nearest RHS 34B; inner set with 1.0 mm margin nearest RHS NN155; both sets with midrib nearest RHS 28B and main portion proximally nearest RHS 19B and distally between RHS 32 C and RHS 32D;

Tepal color (mature abaxial): Inner tepal with 1.0 mm lighter margin of nearest RHS 4D; veins nearest RHS 151D and main portion nearest RHS 13C proximally and nearest RHS 21C distally;

Tepal color (mature adaxial): Inner tepals with 1.0 mm lighter margin of nearest RHS 4D; veins nearest RHS 151D proximally and RHS 17C distally; main portion nearest RHS 11 A proximally and RHS 17C distally;

Androecium: Six, different lengths;

*Filaments*.—Six; terete; glabrous; lustrous; from about 28.0 to 32.0 mm long and about 0.8 mm diameter; color nearest RHS 2C proximally and nearest RHS 1B distally.

*Anther*.—Ellipsoidal, flattened ventrally to dorsally; about 2.0 mm long and 1.5 mm across and 1.0 mm thick; color nearest RHS 9A.

*Pollen*.—Abundant: color nearest RHS 13A.

Gynoecium: Single; about 30.0 mm long;

*Style*.—Terete; glabrous; lustrous; about 25.0 mm long and 0.8 mm diameter: color nearest RHS 1B.

Pedicel: Terete; glabrous; stiff; drooping; about 2.0 mm long and about 0.5 mm diameter;

Pedicel color: Nearest RHS 174A;

Bracts: Lanceolate; subtending individual flowers; with acute apices and truncate base; to about 10.0 mm long and 5.0 mm across at base; average about 5.0 mm long and 2.5 mm across; color blushed with nearest RHS 167B;

Fruit: Tri-valved loculicidal capsule; ovoid-globose; about 8.0 mm long and 8.0 mm across; glabrous; with rounded apex and rounded base; typically four to eight seeded; color upon maturity nearest RHS 199C;

Seed: Irregular with angular sides, acute apex and base; about 4.0 mm and 2.5 mm across; color nearest RHS 200A;

Disease and pest resistance: Resistance beyond that of other *Kniphofia* has not been observed. The plant grows best with good drainage and is able to tolerate some heat when established. Hardiness at least from USDA zone 5b through 9.

I claim:

1. A new and distinct cultivar of Red Hot Poker plant named *Kniphofia* 'Poker Face' as herein described and illustrated.

* * * * *